US012685659B2

(12) United States Patent
Watchmaker et al.

(10) Patent No.: US 12,685,659 B2
(45) Date of Patent: Jul. 21, 2026

(54) ANGULAR DIGITAL ORTHOSIS FOR LOSS OF DISTAL JOINT EXTENSION

(71) Applicants: Greg Watchmaker, Mequon, WI (US); Randy Dahl, Sussex, WI (US)

(72) Inventors: Greg Watchmaker, Mequon, WI (US); Randy Dahl, Sussex, WI (US)

( * ) Notice: Subject to any disclaimer, the term of this patent is extended or adjusted under 35 U.S.C. 154(b) by 224 days.

(21) Appl. No.: 18/233,169

(22) Filed: Aug. 11, 2023

(65) Prior Publication Data

US 2025/0049605 A1     Feb. 13, 2025

(51) Int. Cl.
*A61F 5/01* (2006.01)

(52) U.S. Cl.
CPC .................................. *A61F 5/0118* (2013.01)

(58) Field of Classification Search
CPC ........ A61F 13/12; A61F 13/104; A61F 5/058; A61F 5/05875; A61F 5/0118; A61F 5/10; A61F 5/102; A61F 5/50
USPC ................. 128/869, 879, 880; 602/5, 22, 61
See application file for complete search history.

(56) References Cited

U.S. PATENT DOCUMENTS

| | | |
|---|---|---|
| 293,379 A | 2/1884 | Tower |
| 681,054 A | 8/1901 | Hawley |
| 799,710 A | 9/1905 | Brady |
| 2,548,378 A | 4/1951 | Kleinfeld |

| | | | |
|---|---|---|---|
| 3,039,460 A | 6/1962 | Chandler | |
| 4,441,489 A * | 4/1984 | Evans ................. | A61F 5/05875 602/22 |
| 5,183,458 A * | 2/1993 | Marx ......................... | A61F 5/10 602/30 |
| 5,197,943 A * | 3/1993 | Link ................... | A61F 5/05875 2/21 |
| 5,848,983 A | 12/1998 | Basaj | |
| 6,692,452 B2 | 2/2004 | Chow | |
| D515,216 S | 2/2006 | Weber | |
| D715,951 S | 10/2014 | Stuart | |
| 9,358,148 B2 | 6/2016 | Barnes | |
| 9,872,796 B1 | 1/2018 | Karna | |
| 2009/0099493 A1 | 4/2009 | Barnes | |
| 2009/0204044 A1 * | 8/2009 | Benison .............. | A61F 5/05875 602/22 |
| 2019/0008688 A1 * | 1/2019 | Stojanovski ........ | A61F 13/0206 |
| 2022/0039992 A1 | 2/2022 | Bacik | |

FOREIGN PATENT DOCUMENTS

WO      WO-2021246962 A1 * 12/2021

* cited by examiner

*Primary Examiner* — Caitlin A Carreiro

(57) ABSTRACT

Embodiments of the inventive concepts disclosed herein are directed to an angular digital device for loss of distal joint extension. A device formed from a thin, rigid material shaped to fit the dorsal soft-tissue contour of the middle phalanx of a digit with one or more apex volarly angled distal projections which arise at the level of the distal interphalangeal joint and with a thin sling of material secured to the distal projection(s) by which the volar pad of the distal phalanx is supported in order to provide hyperextension of the distal joint of the digit while maintaining tactile function of the pad of the digit.

7 Claims, 1 Drawing Sheet

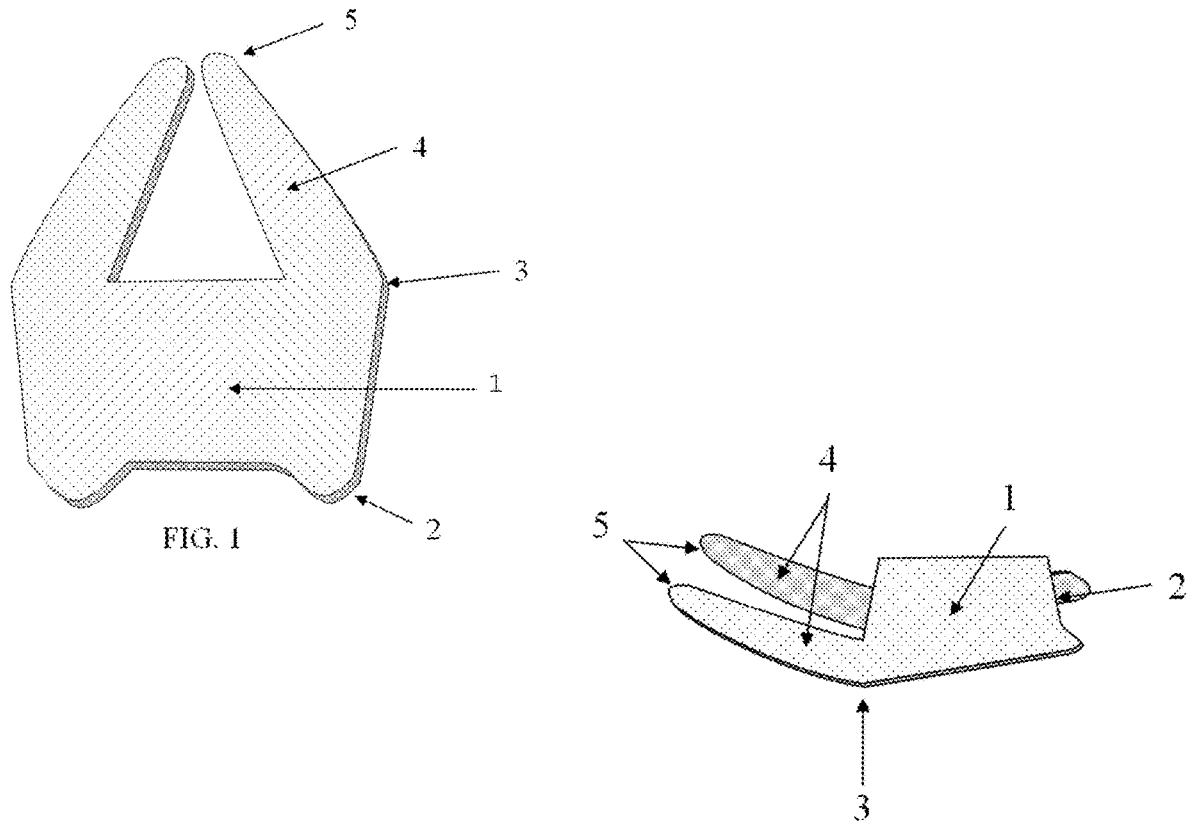
FIG. 1
FIG. 2
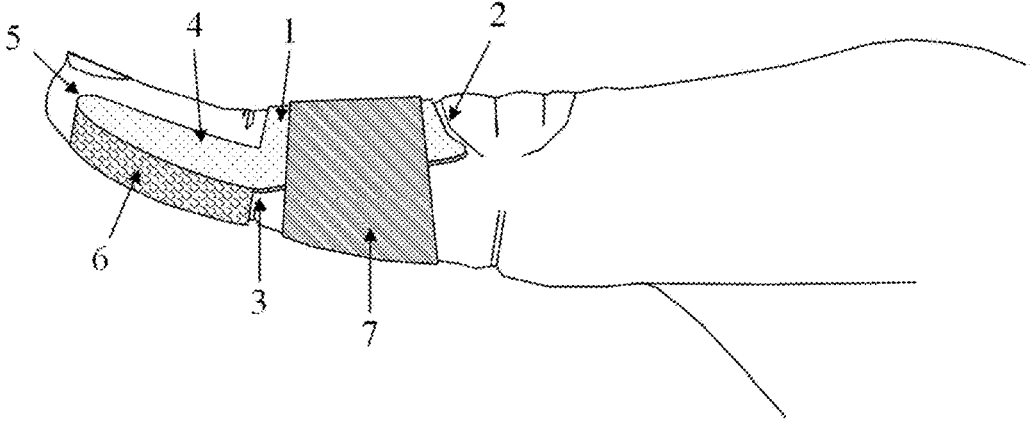
FIG. 3

ANGULAR DIGITAL ORTHOSIS FOR LOSS OF DISTAL JOINT EXTENSION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A READ-ONLY OPTICAL DISC, AS A TEXT FILE OR AN XML FILE VIA THE PATENT ELECTRONIC SYSTEM

Not Applicable

STATEMENT REGARDING PRIOR DISCLOSURES BY THE INVENTOR OR A JOINT INVENTOR

Not Applicable

BACKGROUND OF THE INVENTION

This invention belongs to a class of devices that treat injuries of the distal joint of the digit wherein there is loss of extension of the distal interphalangeal joint (DIP) commonly referred to as a mallet injury. These devices passively maintain the DIP joint in extension during healing of the terminal tendon in a finger or extensor pollicis longus tendon in a thumb.

Previously described devices in this class decrease tactile function of the digit while being worn by virtue of their designs which wrap around the tip of the digit (Barnes 2009, Barnes 2016), or cover a portion of the skin of the finger pad with a rigid or dense material (Kleinfield 1949, Link 1987, Link 1993, Stuart 2014, Wong 2017).

The current invention is novel by overcoming the loss of tactile function of the skin of the finger pad created by these prior designs. The current invention does so by leaving the tip of the digit uncovered by any material of the device and also by using a thin flexible material as the element of the splint which contacts the finger pad.

Prior designs are limited by the manner in which they cross the DIP joint without an apex volarly angled element at the level of the joint (Hawley 1901, Kleinfield 1949, Link 1987, Stuart 2014). Such straight designs allow the DIP joint to partially flex if the splint migrates distally while being worn. This is a common problem when perspiration reduces adhesion of the tape or strap used to secure the splint to the middle phalanx. Straight designs or designs with a gentle bow rather than an angle placed at the level of the joint also allow the DIP joint to flex if the splint does not perfectly fit the size of the digit. The additional room within the splint or distal migration of the splint compromises the intended purpose of maintaining full extension or hyperextension of the DIP joint. Additionally prior designs that purposely place the DIP joint in flexion rather than extension are not intended for treatment of mallet injures (Chandler 1962)

The current invention overcomes prior straight designs by incorporating an apex volar angle to the splint as it crosses the level of the DIP joint. The fixed volar angle of the current invention provides a means for the wearer to achieve a reproducible hyperextension angle across the joint and does not require manipulation of springs or screws as described in prior designs to achieve a desired extension angle.

BRIEF SUMMARY OF THE INVENTION

In one aspect, the embodiments for the inventive concepts disclosed herein are directed to:

A device formed from a thin, rigid material curved to fit the dorsal soft-tissue contour of the middle phalanx of a digit with one or more apex volarly angled distal projections which arise at the level of the distal interphalangeal joint and with a thin sling of material secured to the distal projection(s) by which the volar pad of the distal phalanx is supported in order to provide hyperextension of the distal joint of the digit while maintaining tactile function of the pad of the digit and not encumbering the proximal interphalangeal joint.

BRIEF DESCRIPTION OF THE SEVERAL VIEWS OF THE DRAWING(S)

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings:

FIG. 1 is a top view drawing of the first step in constructing an angular digital device for the distal interphalangeal joint with some embodiments of the inventive concepts disclosed herein.

FIG. 2 is a side drawing demonstrating the second step in constructing an angular digital device for the distal interphalangeal joint with some embodiments of the inventive concepts disclosed herein.

FIG. 3 is a side drawing of the completed construction of an angular digital device for the distal interphalangeal joint with the device applied to a digit with some embodiments of the inventive concepts disclosed herein.

DETAILED DESCRIPTION OF THE INVENTION

Before describing in detail embodiments of the inventive concepts disclosed herein, it should be observed that the inventive concepts disclosed herein include but are not limited to a novel structural combination of components and circuits, and not to the particular detailed configurations thereof. Accordingly, the structure, methods, functions, control and arrangement of components and circuits have, for the most part, been illustrated in the drawings by readily understandable block representations and schematic diagrams, in order not to obscure the disclosure with structural details which will be readily apparent to those skilled in the art, having the benefit of the description herein. Further, the inventive concepts disclosed herein are not limited to the particular embodiments depicted in the schematic diagrams, but should be construed in accordance with the language in the claims.

The device may be used for loss of extensor tendon function of the distal joint of a digit whereby loss of normal motion compromises function. The essential functions of the various embodiments of the device are to provide an extension rotational force centered at the level of the distal interphalangeal joint.

The various elements of the device function through the construction of a thin rigid proximal component contoured to the middle phalanx and one or more apex volar angulated distal extensions to which a thin flexible material is secured which provides volar support to the pad of the digit.

By way of example and referring to FIGS. 1-3, one embodiment of the device may be created from a flat sheet of 0.04" polyester in the illustrated shape that has a proximal component 1 with fabric adhered on one or both sides of the polyester material and with the most proximal edge rounded on each side 2 to comfortably contour to the extension creases of a proximal interphalangeal joint of a digit. From this proximal component of the device arises one or more distal extensions 4 which arise from the proximal component at an angle 3 such that in subsequent construction steps this angle creates an apex volar angle at the level of the DIP joint of the digit. The distal end of the extension(s) 5 are rounded and of a length such that when applied to a digit does not cover the very tip of the digit but instead leaves the sensate tip exposed. A thin, flexible material 6 is secured to the distal extension(s) and is of a contour to support the volar aspect of the finger pad thereby creating an extension force on the DIP joint. Tape or a thin strop 7 is wrapped circumferentially at the level of the middle phalanx to secure the device to the digit.

Terminology

"Volar" refers to the palmar or plantar surface of the hand
"Dorsal" refers to the side opposite the volar surface
"Proximal" refers to closer to the center axis of the body
"Distal" refers to further away from the center axis of the body "Interphalangeal joints" referring to the joints between the proximal, middle, and distal phalanges of the digits of the hand
"Digit" a finger or thumb

What is claimed is:

1. A device configured to produce an extension force at the distal interphalangeal joint of a digit while not encumbering the proximal interphalangeal joint of a digit, the device comprising:

a proximal rigid portion configured to be secured to the middle phalanx and configured for spanning a longitudinal length of greater than one-half the length of the middle phalanx;

a distal rigid portion comprising one or more apex volarly angled distal extensions arising from the proximal rigid portion thereby providing an inclined angle at the joint between the proximal and distal rigid portions;

a thin flexible material secured to the extension(s) configured such that when the device is applied to a digit, a hyperextension force is created at the distal interphalangeal joint.

2. The device as recited in claim 1, wherein the thin flexible material is configured to support the pad of the digit and is configured to readily allow perception of light touch where covered by the material while wearing the device.

3. The device as recited in claim 2, created in various constructions such that the angle between the proximal and distal rigid portions is in the range between 10 and 60 degrees.

4. The device as recited in claim 3, the proximal rigid portion configured to be secured to the skin of the middle phalanx utilizing tape or a strap circumferentially wrapped.

5. The device as recited in claim 4, constructed in various sizes to fit digits of various sizes.

6. A device as recited in claim 5, wherein the thin, flexible material comprises a fabric, mesh, or other thin material configured such that tactile function of the pad of the digit where covered by the material is maintained.

7. A device as recited in claim 1, wherein the thin, flexible material comprises a fabric, mesh, or other thin material configured such that tactile function of the pad of the digit where covered by the material is maintained.

* * * * *